United States Patent [19]

Bongianni

[11] 4,442,714
[45] Apr. 17, 1984

[54] MICROSCOPE AND METHOD OF USE

[75] Inventor: Wayne L. Bongianni, Los Alamos, N. Mex.

[73] Assignee: The United States of America as represented by the United States Department of Energy, Washington, D.C.

[21] Appl. No.: 293,912

[22] Filed: Aug. 18, 1981

[51] Int. Cl.³ ............................................. G01N 29/00
[52] U.S. Cl. ........................................ 73/606; 73/618; 73/643
[58] Field of Search .......................... 73/606, 643, 618

[56] References Cited

U.S. PATENT DOCUMENTS 3,697,867 10/1972 Kleesattel .............................. 73/643
4,011,748 3/1977 Bond et al. .............................. 73/618
4,218,924 8/1980 Fortunko et al. ....................... 73/643

Primary Examiner—Anthony V. Ciarlante
Attorney, Agent, or Firm—Lee W. Huffman; Paul D. Gaetjens; Michael F. Esposito

[57] ABSTRACT

A method and apparatus for electronically focusing and electronically scanning microscopic specimens are given. In the invention, visual images of even moving, living, opaque specimens can be acoustically obtained and viewed with virtually no time needed for processing (i.e., real time processing is used). And planar samples are not required. The specimens (if planar) need not be moved during scanning, although it will be desirable and possible to move or rotate nonplanar specimens (e.g., laser fusion targets) against the lens of the apparatus. No coupling fluid is needed, so specimens need not be wetted. A phase acoustic microscope is also made from the basic microscope components together with electronic mixers.

20 Claims, 7 Drawing Figures

MICROSCOPE AND METHOD OF USE

The invention is a result of a contract with the Department of Energy (Contract No. W-7405-ENG-36).

BACKGROUND OF THE INVENTION

The present invention relates generally to a microscope and to a method of using that device and relates more particularly to an improved acoustic microscope which is capable of real time processing and to methods of using that device.

Today, there is much interest in acoustic microscopy. Using the methods and apparatus which have existed in the prior art, one can observe living cells; and no staining is required.

There are three known types of prior art acoustic microscopes, all of which use piezoelectric transducers. These three types are reflection acoustic microscopes (as disclosed in C. F. Quate, "The Acoustic Microscope," Sci. Am. 241, p. 62 (1979)), transmission acoustic microscopes, and scanning laser acoustic microscopes (SLAM's) (as disclosed in L. W. Kessler er al., "Principles and Analytical Capabilities of the Scanning Laser Acoustic Microscope (SLAM)," Scanning Electron Microscopy/1978/1, An International Review of Advances in Instrumentation Techniques, Theory, and Physical Applications of the Scanning Electron Microscope, Om Johari, Ed., SEM Inc., AMF O'Hare, Il., pp. 555–560. Reflection and transmission acoustic microscopes operate at very high frequencies (within the 1 to 3 gigahertz range) and thus give very good resolution which is comparable to that obtainable with optical microscopes. Both reflection and transmission acoustic microscopes have a focus which is produced by polishing a hemisphere into a material such as sapphire. However, both types require that the object plane move; and the object plane has had to be mechanically moved in order to scan the object. However, if high resolution is desired, one cannot move the object quickly because distortion results as the coupling fluid is disturbed by the motion. Therefore, any mechanical scanning that is done of necessity is very slow. Furthermore, real time processing (i.e., processing in which a specimen can be viewed while it is being scanned) has not been possible with these methods because each image must be stored and the data then later reassembled. Therefore, it has not been possible to view moving objects with these two types of acoustic microscopes.

With the third type of acoustic microscope, the scanning laser acoustic microscope, it has not been necessary to move the object; instead, a laser scans across the acoustic field which passes through a specimen. However, a disadvantage of this type of apparatus is that the frequencies employed of necessity have had to be quite low (on the order of 100 megahertz). Thus, the resolution obtainable has been poor. Additionally, like the two types of acoustic microscopes described above, planar samples are required in the SLAM. All three types require water or some other coupling medium, which introduces loss of signal and wetting of the samples.

Therefore, despite the acoustic microscopes which have existed in the prior art, a need has existed for an acoustic microscope which has simultaneously the advantages of good resolution, no requirement for planar samples, direct coupling to the specimen, and a capability of real time processing (so that the sample can be observed while it is being scanned).

SUMMARY OF THE INVENTION

Objects of this invention are a method and apparatus for electronically focusing a microscopic object.

Other objects of this invention are a method and apparatus for electronically scanning and focusing a microscopic object, using real time processing and without requiring the object to be moved.

Further objects of this invention are a method and apparatus for acoustically obtaining visual images of moving, living objects.

Still further objects of this invention are a method and apparatus for acoustically determining very accurately the thickness of an opaque microscopic object, for example a laser fusion target, within a time period on the order of milliseconds for a given area of the target.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention comprises an acoustic microscope comprising the following items in operable communication: (a) a magnetoelastic transducer to which an rf feed is to be connected; (b) means for producing a biased magnetic field on the magnetoelastic transducer so as to electronically generate a magnetoelastic wave, a part of which wave is an acoustic wave having a wavelength less than about 10 $\mu$m which is generated in response to an rf signal which impinges upon the transducer; (c) means for producing a uniform magnetic field the absolute value of which can be varied in the axial direction so as to physically focus the acoustic wave onto an object and so as to produce a reflected signal reflected by and representative of the object; and (d) means for transducing the reflected signal to a corresponding rf signal which is representative of the object and which can be processed, wherein the means for producing a uniform magnetic field is such that it allows physical contact of the transducer with a specimen being examined and wherein the rf feed to be connected is such that it avoids distorting the acoustic wave.

In a preferred embodiment, the magnetoelastic transducer is a low loss magnetoelastic material capable of magnetoelastic generation and propagation, for example YIG (i.e., yttrium iron garnet), Ga YIG (i.e., gallium-substituted YIG), or lithium ferrite.

In another preferred embodiment, the apparatus includes also an rf signal generator, an rf receiver, and a pressure anvil on which a specimen is placed and which moves the specimen against the transducer.

In another preferred embodiment, the apparatus listed above is operated in cooperation with additional apparatus to provide scanning of the object wherein the object can be placed but need not be moved in order to view a given area.

In yet another preferred embodiment, the apparatus includes (besides items a, b, c, and d, above, and the scanning apparatus) means for mixing the output cw or gated signal with the input cw or gated signal, so as to preserve phase information about the specimen and so as to provide a phase microscope.

The present invention also comprises, in accordance with its objects and purposes, a method of electronically focusing a microscopic object wherein no coupling fluid is needed, the method comprising: (a) transducing an rf signal into a magnetoelastic wave having a spin wave part and an acoustic wave part; (b) physically focusing the produced acoustic wave part of the magnetoelastic wave onto a specimen being observed so as to produce a reflected signal reflected by and representative of the specimen; and (c) transducing the produced reflected signal back to an rf signal, which can then be processed.

Mathematical modeling indicates that by using the magnetoelastic acoustic microscope of the invention, one should be able to obtain quite good focusing (i.e., within 2–3 times the diffraction limit); and the apparatus is also capable of electronic scanning. Additionally, planar samples are not required.

Furthermore, when the magnetoelastic microscope is used with the scanning mechanism, described below, very fast scanning of objects is possible; for example, a surface area of a laser fusion target can be scanned within a time period on the order of milliseconds. Because the objects are scanned electrically, there is virtually no practical upper limit on the scanning speed. Therefore, using the scanning magnetoelastic acoustic microscope, real time processing is possible; and, thus, one can observe the object while it is being scanned. This is of particular importance when the object is alive and is moving.

And, although the focusing capability of the instrument has not yet been optimized, by using a magnetoelastic transducer which can be influenced by magnetic fields and by controlling the magnetic field electronically, one can both focus and scan the microscopic object electronically.

Other advantages of the invention include direct coupling to the specimens without the need for an intervening coupling fluid. Hence, the sample need not be wetted by a fluid.

Although magnetoelastic transducers have been used in delay line work with radar involving electromagnetic radiation which is propagated over a distance of thousands of kilometers, magnetoelastic transducers have not previously been used in any type of microscope. It is believed that radar devices and microscopes are quite different fields of art and that it was unobvious to use this type of transducer with acoustic signals to look at microscopic objects.

It was doubtful that the transducer would work in a microscope. When an rf wave at a frequency of 1 gigahertz in free space is generated, the wave is about 1 foot long. This is a huge dimension as compared with the size of an acoustic wavelength. Therefore, there was a question of whether enough energy could be focused into an area measuring micrometers on a side.

The coupling is not simple coupling. When a biased magnetic field is applied to a magnetoelastic transducer (i.e., a material capable of magnetoelastic generation and propagation) many atomic dipoles (which make up the unpaired electron spin) are aligned. An rf field applied at right angles to the magnetoelastic transducer will tend to cause the atomic dipoles to rotate at right angles, thus forming the so-called backward magnetostatic wave (which in this case is a magnetoelastic wave). When that wave reaches a portion of the magnetoelastic transducer called the "launch surface" (which represents a minimum energy surface within the material), the wave tends to be reflected and results in a spin wave (sometimes called a magnetostatic wave). At a point called the "crossover" the spin wave converts to an acoustic wave. Although Addison et al. (in J. Appl. Phys., Vol. 39, no. 3, pp. 1827–1839, February 1968) knew in their delay line work that one could focus the spin wave, it had not previously been known whether a focused spin wave would then carry over to an acoustic wave and whether that acoustic wave would then be in focus. Additionally, it was not known whether this was possible at the surface of a specimen. Bongianni (J. Vac. Sci. Technol., Vol. 18, no. 3, pp. 1214–1217 (April 1981) extended their theoretical work to the acoustic wave and demonstrated that a focused acoustic spot at the surface with a spot size of 25 μm should be achieved at 1.5 GHz.

BRIEF DESCRIPTION OF THE DRAWINGS

The accompanying drawings, which are incorporated in and form a part of the specification, illustrate various embodiments of the present invention and, together with the description, serve to explain the principles of the invention. In the drawings.

DESCRIPTION OF THE PREFERRED EMBODIMENTS

Figure 1:
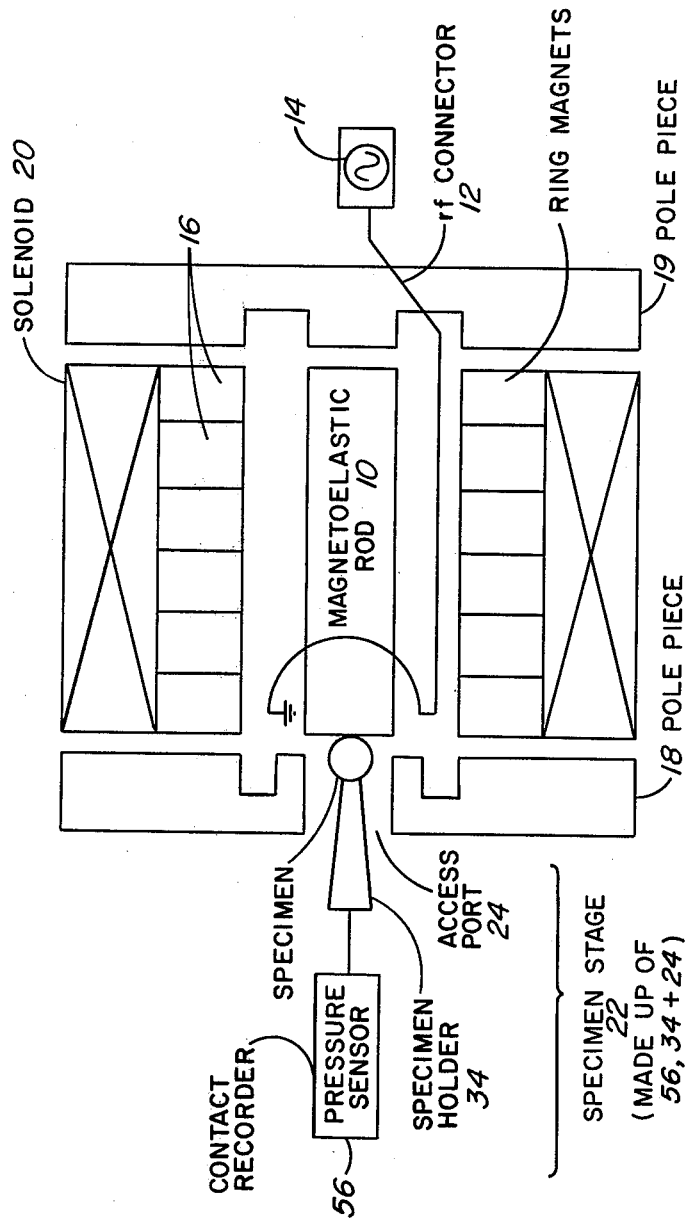
In FIG. 1 an embodiment showing the basic components of a magnetoelastic acoustic microscope of the invention (without the scanning apparatus) is illustrated in cross-section. The lens of the microscope is the magnetically biased rod.

Referring to the drawing, in FIG. 1 the basic components of an embodiment of a magnetoelastic acoustic microscope according to the invention are shown in cross-section. The components are assembled symmetrically about an axis, at the center of which is located a magnetoelastic material in the shape of a rod 10, which (when it is magnetically biased parallel to the axis) generates and propagates magnetoelastic waves. Such a material is required in the practice of the invention. Located at some position within the material is a magnetic equipotential surface (called a launch surface) to which an rf field will ultimately couple and at which the incoming rf waves (which are electromagnetic) will ultimately be converted to acoustic waves.

Various materials of this type can be used, including for example yttrium iron garnet (i.e., YIG), gallium-substituted YIG, and lithium ferrite. However, the most important material of this type is a single crystal YIG which is low loss (i.e., which combines low spin wave resonance loss with a very low elastic wave loss); therefore, YIG is the preferred magnetoelastic material to be used at this time.

Also shown in FIG. 1 is an rf connector 12 which is grounded across the magnetoelastic rod 10 and which couples a source of alternating current at rf frequencies to the magnetoelastic material.

Surrounding the magnetoelastic rod 10 are a multiplicity of adjacent ring magnets 16 and pole pieces 18 and 19. These serve to magnetically bias the magnetoelastic rod. Surrounding these magnets is a solenoid 20 which would be connected to a dc power supply (not shown). The solenoid acts as a focus control for the microscope, the launch surface physically moving when the magnetic field is changed. (The frequency of the applied rf field also moves the launch surface.) This operation is very similar to the adjustment for changing the distance between a lens and an object being observed in an optical microscope. A specimen stage 22 allows a specimen to be placed into physical contact with magnetoelastic rod 10. The stage 22 consists of an access port 24 hollowed out within pole piece 18, a specimen holder (i.e., pressure anvil 34) which holds the specimen against the face of rod 10, and a pressure sensor (i.e., pressure meter 56) which records when intimate contact is made.

Alternately, if desired, although not preferred, the functions of magnets 16 and solenoid 20 (described above) can both be furnished by a single solenoid. In this event, pole pieces 18 and 19 might not be needed. However, this alternative would require the use of more power, would heat the sample being examined, and would cause the focus to drift.

The operation of the apparatus shown in FIG. 1 is the following. A microwave (an rf wave having a frequency in the microwave region) signal enters the magnetoelastic material, is launched from its launch surface, is converted to an acoustic wave, and is focused onto the specimen (provided that the launch surface is at the correct physical position for such focusing). Then, the specimen reflects the focused acoustic wave in a way depending upon the properties of the specimen. Thus, the incoming electromagnetic wave is transduced to an acoustic wave by the magnetoelastic material. Then the acoustic wave which has been reflected by the specimen is transduced into an output rf wave. By comparing the input signal and the output signal, much information can be obtained about the appearance and properties of the specimen being examined.

Figure 2:
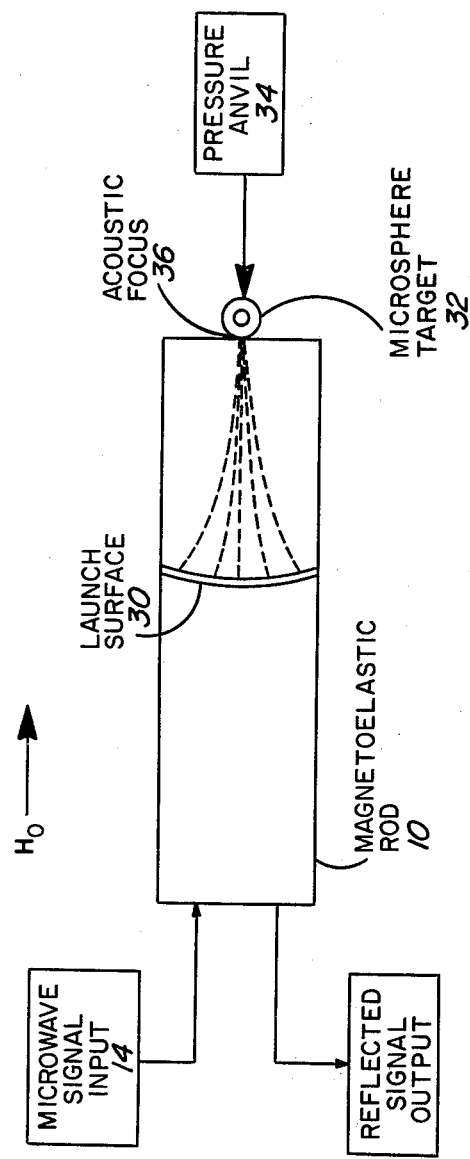
In FIG. 2 is an embodiment illustrated in cross-section showing the basic microscope (again without the scanning apparatus and without showing the pole pieces), the positioning of an object when it is being observed, and the input and output signals.

In FIG. 2, the apparatus of FIG. 1 is shown in detail, together with a specimen being examined (which is here a microsphere target), representations of the input and output signals, and the applied magnetic field. Within the magnetoelastic rod 10, the launch surface 30 is shown, although this surface is not actually physically visible. Microsphere target 32 is pressed by pressure anvil 34 against the center of rod 10 at the end which is opposite the microwave signal input. The acoustic focus 36 is located at that position when the magnetic field and frequency of the ac field are appropriately chosen. The magnetic field $H_O$ represents the field necessary to focus the acoustic wave onto, or into, the sample (which is here a hollow target). The dotted lines represent the acoustic wave.

The apparatus shown in FIGS. 1 and 2 differs in the following ways from apparatus which would be used in delay line work. In the present invention, a surface of the magnetoelastic material is accessible to a specimen, the lens having an exposed face against which the specimen is pressed. This exposed face is permitted by use of a solenoid 20 and by use of a hollow pole piece for producing a uniform magnetic field; whereas in delay line work, the design would employ solid pole pieces across both faces of the crystal and it would not be possible to place a sample at either face. Furthermore, in delay line work, there is no sample. In the present invention, because of that exposed face, the strong fields which are required for delay line work are degraded and the uniformity of the field is lessened. Therefore, this design would probably not be suitable for delay line work. Additionally, delay line apparatus would not make use of a stage (i.e., a pressure anvil) as used with the present invention. Furthermore, the geometries of these systems are quite different; for example, in delay line work the rf wire traverses the center of the rod face. Since this would interfere with sample contact in the present invention, the wire is displaced off-center. Alternatively, it can consist of a strip of thin film vacuum deposited on a diameter on the face of the rod. (The vacuum deposited material can be, for example, a 1000 Å thick film of gold deposited onto a 50 Å film of chromium deposited onto the face of rod 10.) These two measures have provided satisfactory experimental results. Other contemplated alternatives include placing a drop of fluid (for example, water) on the face of the rod, inserting the rf feed through the drop of water, and placing the specimen in contact with the drop, thus making use of a longitudinal wave (described below). Another possibility is to place the rf feed at a distance within rod 10 beyond the launch surface (so that the rf feed is not between the specimen and the launch surface).

Additionally x and y coils would not be used in delay line work because scanning would not be used. Furthermore, the method of operation of the microscope of the present invention is quite different from that of delay line apparatus wherein only a collimated (not focused) beam is desired.

The invention, therefore, uses a magnetoelastic transducer (i.e., a magnetoelastic crystal) in a new way; i.e., in a microscope.

Figure 3:
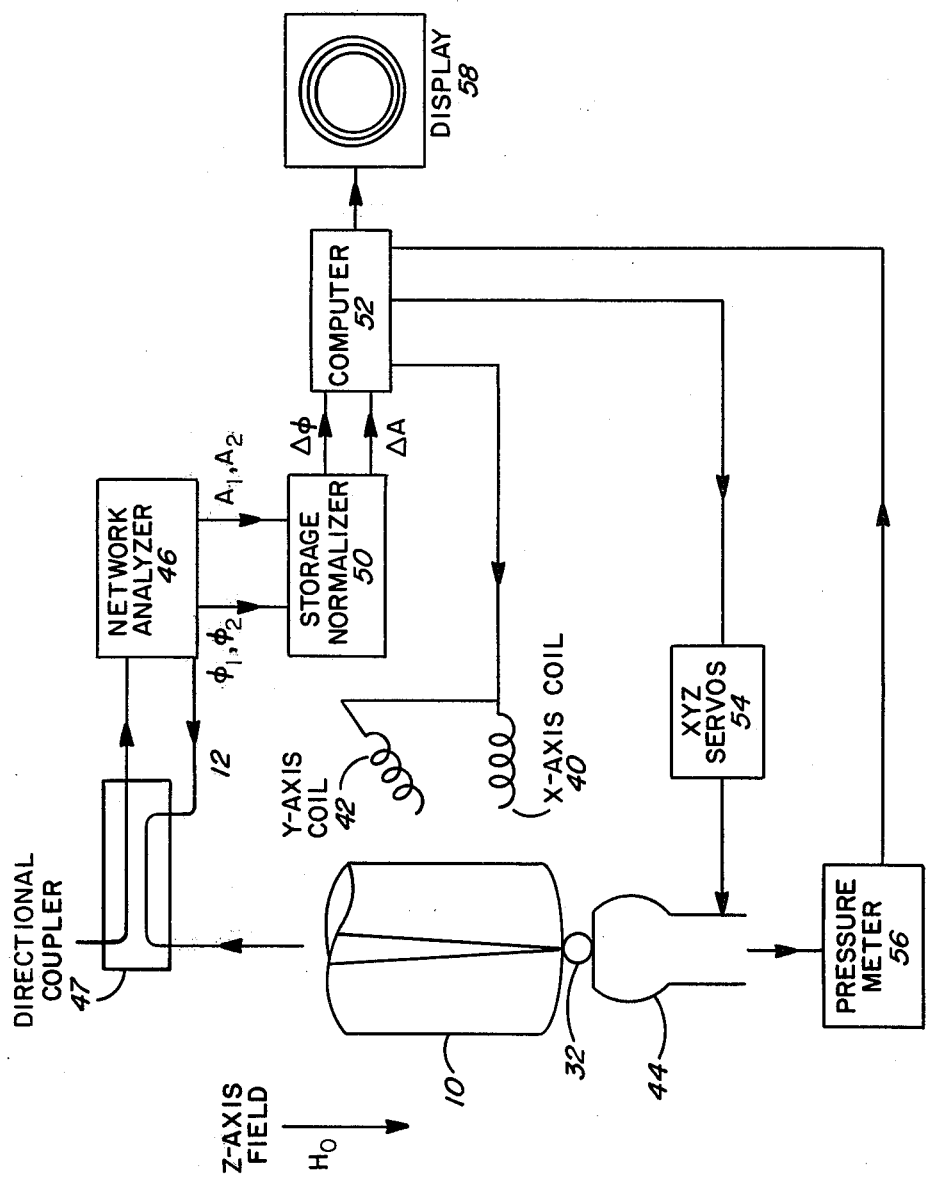
In FIG. 3 a schematic diagram of an embodiment of a scanning magnetoelastic acoustic microscope is shown, including the parts of the apparatus which provide the scanning and the apparatus parts which can be used for processing the output signal.

In FIG. 3, apparatus which can be used to produce a scanning magnetoelastic microscope is shown schematically.

The magnetoelastic rod 10 is aligned in the z direction field with its axis parallel to that field. Then, two orthogonal fields produced by an x-axis coil 40 and a y-axis coil 42 (shown spaced apart from rod 10 in FIG. 3 for clarity) which are both wrapped around the rod provide electronic manipulation of the acoustic wave in the x and y directions, thus providing a scanning mechanism for the device. A microsphere target 32 is shown positioned between one end of magnetoelastic rod 10 and a pressure anvil 44, which can be moved in the x, y, and z directions by a suitable device (described below). A network analyzer 46, which emits an rf signal, which compares that rf signal with a reflected signal from the specimen, and which analyzes both signals, is operatively connected to a directional coupler 47 (which is also called a hybrid and which can alternatively be substituted by a circulator) is able to discriminate on the basis of the direction in which an electrical wave is moving. The emitted rf signal passes into the magnetoelastic rod 10 through the rf connector 12, which is grounded around the crystal (i.e., rod 10).

Network analyzer 46 then compares the input and output rf signals, provides analysis in either a phase or amplitude mode, and feeds that information into a storage normalizer 50, which normalizes the signal to the signal obtained without the sample. The output from storage normalizer 50 is information of a phase change or an amplitude change, and this is sent into computer 52. Computer 52 is operatively coupled, if desired, to x-axis coil 40 and y-axis coil 42. Computer 52 can be also operatively coupled to an xyz servo 54, which automates the motion of pressure anvil 44 in all three dimensions, if automation is desired. If desired, an output from a pressure meter 56 (which measures the pressure exerted by pressure anvil 44 on target 32) can be sent to computer 52. An output from computer 52 is sent to display 58 for visualization of properties of the target.

Figure 4:
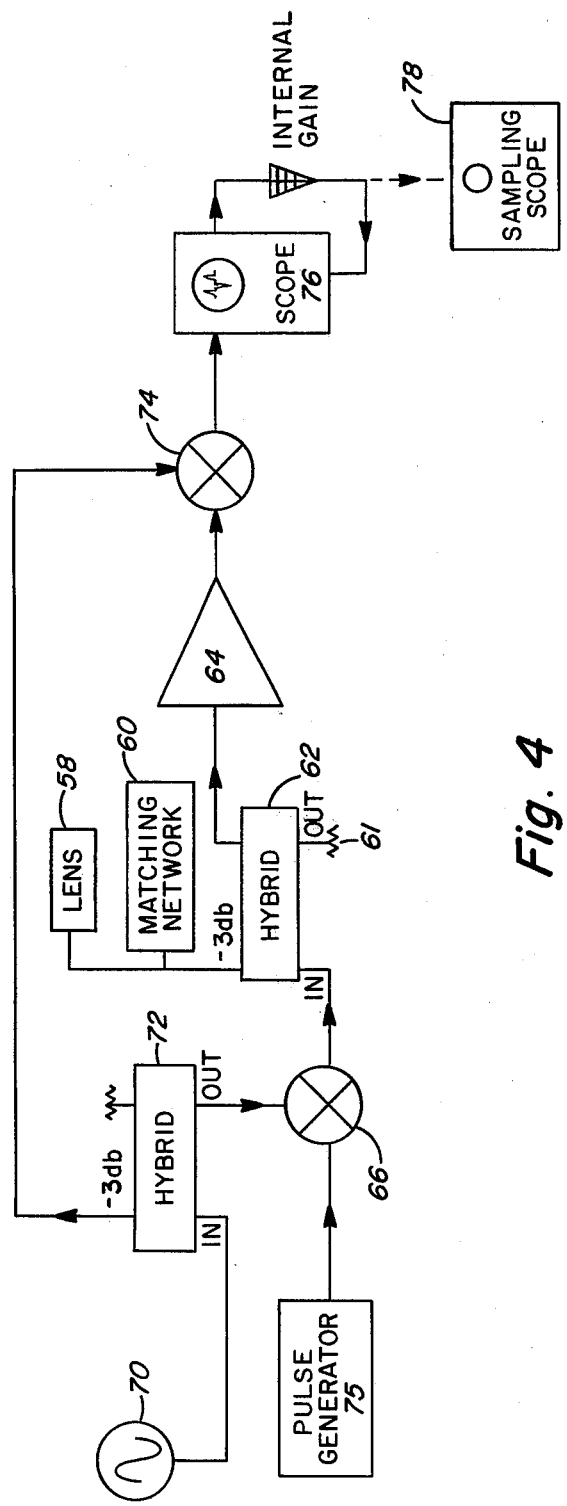
In FIG. 4 is shown an embodiment of a phase sensitive detector which plots phase shift versus acoustic focus position on the sample, thus providing a phase acoustic microscope which gives an extremely sensitive measurement of the thickness of a sample.

In FIG. 4, an embodiment utilizing a lens 59 of the invention to provide a phase microscope is shown. The lens is operatively coupled to a matching network 60 which matches the lens to the electrical circuit in order to minimize the electrical losses. This matching network can be, for example, a quarter wave stub for tuning the lens over a certain frequency range. Alternatively, other devices such as a half wave transformer can be substituted for the quarter wave stub.

The phase detection network works as follows: an rf signal source 70 provides a signal to a −3 db hybrid 72 which splits the signal into two arms. In one arm, the reference arm, the signal proceeds to the second mixer 74, and there provides the reference signal. The other half of the signal proceeds down the analysis arm to the mixer 66, and the signal may be gated to any appropriate length including cw (continuous wave where no gating at all is used). The length and timing of the gate is provided by the pulse generator 75 shown. The gated signal now proceeds through the hybrid 62 where half of the signal is directed into the lens 59 by way of the matching network 60. The other half is absorbed in a load 61, preventing any direct signal from propagating into the circuit. The signal which is reflected from the lens 59 proceeds back through the matching network 60 and out the fourth port of the hybrid 62 and into the amplifier 64. The analysis signal is amplified by amplifier 64 until its strength is comparable with the signal in the reference arm. The signal then enters the mixer 74 and "mixes" with the reference signal, producing a signal of which the amplitude is proportional to the phase difference between the two arms. The output from mixer 74 is then fed into a scope 76 for visualizing the electrical signals which are representative of the sample being analyzed. Scope 76 can be, for example, a Tektronix 484 scope. If additional sensitivity is needed, that scope 76 can be operatively coupled, if desired, into a sampling scope 78, which can detect very high frequency signals, which requires no amplifiers to provide signal details, and which can be used to take photographs of the displayed signals representative of the sample being analyzed.

In the apparatus schematically represented in FIG. 4, if desired, one can use a commercially available apparatus to replace all of the parts shown except for the lens 58 and the matching network 60. A suitable apparatus is a Hewlett Packard microwave network analyzer.

The variable axial field which controls the focus can be varied in a number of ways, including varying the position of the solenoid or the magnet by mechanically moving the coil or magnet. However, this method is not preferred because of the problems associated with mechanical movement. Alternatively, it is believed that it may be possible to vary the direction of the field for this purpose. However, although this may bend the field, it also may defocus it. This alternative has not yet been fully investigated. The preferred way of carrying out this function is to vary the magnitude of the magnetic field. This method is preferred because it is the simplest method, does not perturb the microwave signal, and does not involve mechanical displacements which are time consuming.

Instead of these alternatives, although not preferred, it is believed that it may be possible to vary the frequency of the rf signal to change the position of the focus, using a fixed field. However, this alternative is not preferred because if the frequency is changed, rematching of the system must then be done.

It is believed that by increasing the strength of the axial magnetic field, such as by using very strong magnets (for example, commercially available samarium cobalt magnets), the focusing ability of the lens can be improved. In order to obtain the results shown in FIGS. 5, 6, and 7, a magnetic field of about 1000 gauss produced by Alnico VIII magnets and a frequency of 935 MHz for the particular YIG crystal (which had a length to diameter ratio of 10 to 3) were used and gave mild focusing. However, it is believed that other combinations of these parameters may result in an even better focusing.

Additionally, although the crystal was in the shape of a cylinder, it is believed that other geometries (unknown at this time) might be found to give even better results. However, it is believed that using spherical geometry would not give satisfactory results because such a geometry would not provide a magnetic field gradient (which is required for the operation of the apparatus).

It is believed that a possible improvement in the present device might result from using a corner cube or a polarization reversal crystal (i.e., a half plate) which would allow the produced signal to be reflected from a surface of the corner cube or polarization reversal crystal to the other end of the crystal. This design would permit the entire length of the crystal to act as a lever arm and this could have the advantage of allowing a very small deflection field to be used.

It is desired that when scanning is to be done, the beam should be deflected as much as possible with as little applied energy as possible. This is so because any applied field will tend to change the axial field; and this change must then be compensated for. However, if the beam is swept with very small fields, the focus will be maintained while the beam is moved.

Although a magnetoelastic crystal in the shape of a rod is preferred at this time, if (on the other hand) a misaligned direction (i.e., the rod axis oriented for example 20° from the <100> axis in the (001) plane) of the crystal were employed, it is believed that it could be possible to generate a longitudinal wave. Then, this wave could focus into a liquid, yielding a capability which is not yet possible in the apparatus (described below) which has been built.

It is also believed that using a multiple element magnetoelastic lens might give improved results.

For an applied magnetic field of 1500 gauss and a frequency of 1.5 GHz, it has been calculated that the best focusing will result when the launch surface is within 5% of the physical surface. Although this appears to be a critical feature, it is not fully understood at this time.

EXAMPLE

Apparatus was assembled substantially as shown in FIGS. 1, 2, 3 and 4 (except that an x-axis coil 40, a y-axis coil 42 and an xyz serbos 54 were not employed). A single YIG crystal in the shape of a cylinder was the magnetoelastic transducer (i.e., rod 10). The length of rod 10 was 1 cm and the width was 3 mm. Crucible R835 ring magnets (which were Alnico VIII magnets obtained from Crucible Steel) were positioned axially around rod 10 as shown in FIG. 1 so that they formed a uniform field in the region of the rod. The field was about 1000 gauss. The solenoid was a wire wound about a form machined from plexiglass. An rf connector and a 0.25 mm diameter wire were used to provide access of the rf signal to the device. These items formed lens 58 in FIG. 4.

The rf signal was generated by a HP8754A network analyzer and had a frequency of 935 MHz. The matching network 60 was a quarter wave stub, which was built from coax connectors. Directional coupler 62 was a $-3$ db directional hybrid, purchased from Omni Spectra. Amplifier 64 was an Avantek UTC-10-108M. Mixer 66 was Lorch FC-2357; and mixer 74 was Lorch FC-2357. Scope 76 was a Tektronix 484. A Hewlett Packard sampling scope was used to improve sensitivity and to obtain photographs of the displayed signals.

Figure 5:
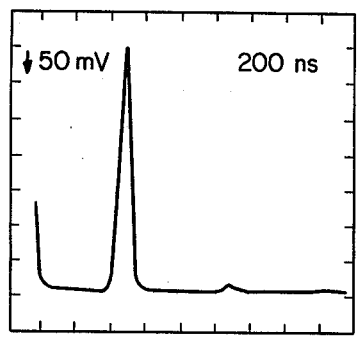
In FIGS. 5–7, experimental results which were obtained by using an apparatus substantially as shown in FIG. 2 are given. Items shown in several figures are numbered the same.

In FIG. 5 is shown the actual experimental response of a YIG crystal (with no sample present) to an applied rf pulse (at a frequency of 935 MHz, and applied field from the solenoid and the magnets of approximately 1100 gauss), showing the first, second, and third echoes to the right of the input pulse. These are echoes which result within the crystal itself due to its physical boundaries and the interaction of those boundaries with the applied pulse. The amplitude of the first echo was 350 millivolts and the delay time was 600 ns.

Figure 6:
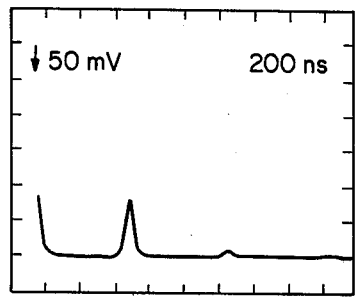

In FIG. 6 is shown the response of that same crystal to that same pulse when a specimen is present and when much energy is entering the sample. The first echo can be observed to be severely attenuated, but the second and third are not significantly affected.

Figure 7:
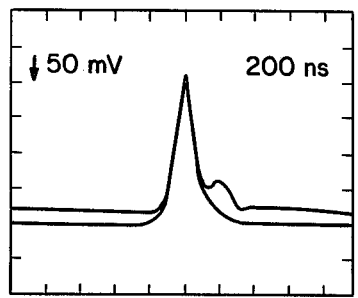

In FIGS. 5 and 6, each unit on the ordinate corresponds to 50 mV and each unit on the abscissa corresponds to 200 ns. In FIG. 7, these are respectively 50 mV and 50 ns.

In FIG. 7, two superimposed photographs are shown. One of these is of an object (a Chamisa target which is a laser fusion sample, having a diameter of 1.5 mm and made of a BeCu sphere) plated with 1.5 mils of gold. The other superimposed photograph is of an echo without the sample in contact. In each case, the applied pulse was 500 millivolts and the applied pulse duration was 150 ns. This photograph is extremely significant in that it is the first picture which was ever obtained showing reflection off something other than the YIG rod. The distance between the two peaks in the photograph gives a measure of the thickness of the plated film, which was measured to be 1.2 mils±0.12 mil.

For determining thickness, if desired a planar sample having a known thickness can be used for calibration. Alternatively, if the speed of sound is known in the particular material being examined, no calibration is required.

Although an apparatus having a scanning capability has not yet been built, computer modeling indicates that it is feasible.

The foregoing description of preferred embodiments of the invention has been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An acoustic microscope comprising in operable communication:
    (a) a magnetoelastic transducer to which an rf feed is to be connected wherein said transducer is in the shape of a rod which has an axis of symmetry;
    (b) means for producing a magnetoelastic wave within said magnetoelastic transducer, a part of which wave is an acoustic wave having a wavelength less than about 10 $\mu$m which is generated in response to an rf signal which impinges upon said transducer;
    (c) means for producing a uniform magnetic field the absolute value of which can be varied along said axis of symmetry of said rod so as to physically focus said acoustic wave onto a specimen and so as to produce a reflected signal reflected by and representative of said specimen; and
    (d) means for transducing said reflected signal to a corresponding rf signal which is representative of said specimen and which can be processed, wherein said means for producing a uniform magnetic field is such that it allows physical contact of said transducer with a specimen being examined and wherein said rf feed to be connected is such that it avoids distorting said acoustic wave.

2. An apparatus according to claim 1, wherein said magnetoelastic transducer comprises at least one low loss material capable of generating and propagating magnetoelastic waves and wherein said apparatus includes also an rf feed selected from the group consisting of a separate rf feed which is placed off-center with respect to said transducer and an rf feed which is a thin strip of conductive film located on one end of and passing along a diameter of said transducer.

3. An apparatus according to claim 2 and including also an rf signal generator and an rf signal receiver and a pressure anvil on which said specimen is placed and which moves said specimen against said transducer.

4. An apparatus according to claim 3, wherein said means for producing a uniform magnetic field the absolute value of which can be varied along the axis of symmetry of said rod is a means which varies the magnitude of said axial magnetic field.

5. An apparatus according to claim 4, wherein said low loss material is selected from the group consisting of yttrium iron garnet, gallium-substituted yttrium iron garnet, and lithium ferrite.

6. An apparatus according to claim 5, wherein said low loss material is yttrium iron garnet.

7. Apparatus according to claim 4, wherein said means for producing a uniform magnetic field is a solenoid and wherein said means for transducing said reflected signal to a corresponding rf signal is said magnetoelastic transducer.

8. Apparatus according to claim 7, wherein said means for producing a magnetoelastic wave is a multiplicity of adjacent ring magnets and pole pieces.

9. An electronically scanning acoustic microscope comprising the apparatus according to claim 1 or claim 2 and including also means for applying two orthogonal magnetic fields to said magnetoelastic transducer so as to provide scanning of a specimen.

10. A phase acoustic microscope comprising the apparatus of claim 9 and including also an rf mixer which mixes an rf input signal with an rf output signal so as to preserve phase information concerning a sample which is being examined.

11. A method of electronically focusing an object which is microscopic in size and wherein no coupling fluid is needed, said method comprising:
(a) passing an rf input signal into a magnetically biased magnetoelastic material which transduces said rf input signal within said material into a magnetoelastic wave made up of a spin wave and an acoustic wave:
(b) physically focusing said acoustic wave part of said magnetoelastic wave onto said object so as to produce a reflected signal reflected by and representative of said object; and
(c) transducing said reflected signal back to an rf output signal, which can then be processed.

12. A method according to claim 11, wherein said magnetically biased magnetoelastic material is a low loss ferromagnetic material capable of magnetoelastic generation and propagation.

13. A method according to claim 12, wherein said magnetically biased ferromagnetic material is selected from the group consisting of yttrium iron garnet, gallium-substituted yttrium iron garnet, and lithium ferrite.

14. A method according to claim 13, wherein said magnetically biased ferromagnetic material is yttrium iron garnet.

15. A method according to claim 14 or claim 9 and including also the step of applying two orthogonal magnetic fields to said ferromagnetic material so as to provide scanning of said object.

16. A method according to claim 14 and including also the step of processing said rf output signal.

17. A method according to claim 16, wherein said rf output signal is mixed with said rf input signal so as to preserve phase information concerning said object.

18. Apparatus for electronically focusing a microscopic object wherein no coupling fluid is needed, said apparatus comprising:
(a) means for transducing an rf signal into a magnetoelastic wave having a spin wave part and an acoustic wave part;
(b) means for physically focusing said produced acoustic wave part of said magnetoelastic wave onto a specimen being observed so as to produce a reflected signal reflected by and representative of said specimen; and
(c) means for transducing said produced reflected signal back to an rf signal, which can then be processed.

19. A method of electronically focusing a microscopic object wherein no coupling fluid is needed, said method comprising:
(a) transducing an rf signal into a magnetoelastic wave having a spin wave part and an acoustic wave part;
(b) physically focusing said produced acoustic wave part of said magnetoelastic wave onto a specimen being observed so as to produce a reflected signal reflected by and representative of said specimen; and
(c) transducing said produced reflected signal back to an rf signal, which can then be processed.

20. A method according to 19, wherein said transducing is performed by a magnetoelastic transducer to which an rf feed is to be connected and wherein said focusing is performed by a solenoid.

* * * * *